(12) United States Patent
Singer

(10) Patent No.: US 8,309,091 B2
(45) Date of Patent: Nov. 13, 2012

(54) CEACAM8-RELATED METHOD FOR TREATING AUTOIMMUNE DISEASES

(75) Inventor: Bernhard Singer, Essen (DE)

(73) Assignee: Charite-Universitatsmedizin Berlin, Berlin (DE)

( * ) Notice: Subject to any disclaimer, the term of this patent is extended or adjusted under 35 U.S.C. 154(b) by 581 days.

(21) Appl. No.: 12/084,390

(22) PCT Filed: Oct. 31, 2006

(86) PCT No.: PCT/EP2006/067999
§ 371 (c)(1), (2), (4) Date: Apr. 30, 2008

(87) PCT Pub. No.: WO2007/051805
PCT Pub. Date: May 10, 2007

(65) Prior Publication Data
US 2009/0130116 A1    May 21, 2009

(30) Foreign Application Priority Data

Nov. 1, 2005 (EP) .................................. 05090302

(51) Int. Cl.
*A61K 39/395* (2006.01)
*C07K 16/28* (2006.01)
(52) U.S. Cl. ............... 424/153.1; 424/130.1; 424/141.1; 424/173.1; 530/387.1; 530/388.1; 530/388.2; 530/388.7
(58) Field of Classification Search .................. None
See application file for complete search history.

(56) References Cited

U.S. PATENT DOCUMENTS

| | | | |
|---|---|---|---|
| 5,877,295 A * | 3/1999 | Diamond et al. | 530/388.73 |
| 6,117,985 A * | 9/2000 | Thomas et al. | 530/413 |
| 7,132,255 B2 * | 11/2006 | Blumberg | 435/29 |
| 7,541,440 B2 * | 6/2009 | Goldenberg et al. | 530/387.3 |
| 2004/0185053 A1 | 9/2004 | Govindan | |
| 2004/0214184 A1* | 10/2004 | Skubitz et al. | 435/6 |
| 2010/0284976 A1 | 11/2010 | Schendel et al. | 424/93.7 |
| 2011/0003710 A1 | 1/2011 | Konstantopoulos et al. | 506/9 |

FOREIGN PATENT DOCUMENTS

| | | |
|---|---|---|
| WO | WO 99/52552 | 10/1999 |
| WO | WO 01/13937 | 3/2001 |
| WO | WO 02/068601 | 9/2002 |
| WO | WO 03/002764 | 1/2003 |
| WO | WO 2004/029093 | 4/2004 |

OTHER PUBLICATIONS

Oostrom et al., Journal of Medicine 62: 320-325, 2004.*
Honig et al., Journal of Leukocyte Biology 66: 429-436, 1999.*
Rubel et al., Journal of Immunology 166: 2002-2010, 2001.*
AbD Serotec DataSheet for MCA2167 (80H3) obtained Jul. 6, 2011 from www.abdserotec.com/catalog/datasheet-MCA2167.html.*
Torsteinsdottir et al., Enhanced Expression of Integrins and CD66b on Peripheral Blood Neutrophils and Eosinophils in Patients with Rheumatoid Arthritis, and the Effect of Glucocorticoids, XP-002373716, *Scand. Journal of Immunol.* 50, 433-439 (1999).
Singer et al., CEACAM1 (CD66a) mediates delay of spontaneous and Fas ligand-induced apoptosis in granulocytes, *Eur. J. Immunol.* 2005 35:1949-1959.
Mannoi et al., 1982, Human Immun. 5:309-323.
Daniels et al., 1993, Int. J. Cancer 55:303-310.
Dellagi et al., 1983, EMBO J. 2(9)1509-1514.
Dellagi et al., 1985, Blood 65:1444-1452.
Wakasugi et al., 1984, J Immunol. 132(6):2939-2947.
Pebusque et al., 1988, Blood 72:257-265.
Bernard et al., 1984, Bulletin of the World Health Organization, 62 (S):809-811.
Lanza et al., 1994, Haematologica 79:374-386.
HLDA Antibody Database 1998 [online][retrieved on May 14, 2012].
Kuroki et al., J Leukocyte Biol. 1992, 53:551-557.
Kuijpers et al., 1992, J Cell Bio. 118(2):457-466).
Binet et al., 2008, J Leukocyte Biol. 84:1613-1622.
Bankey et al., 2010, Immunol Lett. 129(2):100-107.
Guervilly et al., 2011, Critical Care 15:R31.
GeneWay sale of mAB80H3 [online][retrieved May 14, 2012]retrieved from the Internet.
LifeSpan Biosciences sale of mAB80H3, May 9, 2012 [online][retrieved May 14, 2012]retrieved from the Internet.
Novus Biologicals sale of mAB80H3, Feb. 22, 2012 [online][retrieved May 14, 2012]retrieved from the Internet.
Thermo Scientific sale of mAB80H3, 2012 [online][retrieved May 14, 2012]retrieved from the Internet.
Serotec terms and conditions of sale of mAB80H3, Mar. 15, 2012 [online][retrieved May 14, 2012]retrieved from the Internet.
LifeSpan Biosciences terms and conditions of sale of mAB80H3, 2012 [online] [retrieved May 14, 2012]retrieved from the Internet.
Product description from Beckman Coulter 2011 [online][retrieved May 14, 2012]retrieved from the Internet.
Guidance for Industry and FDA Staff Commercially Distributed Analyte Specific Reagents (ASRs): Frequently Asked Questions, Sep. 14, 2007.

* cited by examiner

*Primary Examiner* — Phillip Gambel
(74) *Attorney, Agent, or Firm* — VLP Law Group LLP

(57) ABSTRACT

The invention relates to the use of substances which are specific to CEACAM8 for the manufacture of a medicament for the prophylactic or therapeutic treatment of human autoimmune diseases and/or gout. Another object of the invention concerns the use of CEACAM8-specific substances for apoptosis induction in-vitro. The invention also relates to a method for screening substances which induce apoptosis and a method for inducing apoptosis in human granulocytes.

2 Claims, 5 Drawing Sheets

CEACAM8-RELATED METHOD FOR TREATING AUTOIMMUNE DISEASES

PRIORITY CLAIM

This is a U.S. national stage of application No. PCT/EP06/067999, filed on Oct. 31, 2006. Priority is claimed on the following application(s): Country: Europe, Application No.: 05090302.0, Filed: Nov. 1, 2005; the content of which is incorporated here by reference.

BACKGROUND OF THE INVENTION

The invention relates to the use of substances which are specific to CEACAM8 for the manufacture of a medicament for the prophylactic or therapeutic treatment of human autoimmune diseases and/or gout. Another object of the invention concerns the use of CEACAM8-specific substances for apoptosis induction in-vitro. The invention also relates to a method for screening substances which induce apoptosis and a method for inducing apoptosis in human granulocytes.

Granulocytes form the first and fastest line of defense against pathogenic infections. Upon arrival at the site of infection, they participate in the inflammatory reaction by phagocytosis and intracellular killing of bacteria, the production of inflammatory mediators and the release of cytotoxic enzymes and proteins. An unfortunate consequence of granulocyte recruitment represents the ability to cause collateral tissue damage during acute inflammation, and thus their activity and their half-life must be tightly controlled. Their survival is limited by apoptosis, a process that is critical for the resolution of inflammation. Apoptosis refers to a programmed cell death, whereby the cell executes a cell's intrinsic suicide program. It is thought that the apoptosis program is evolutionarily conserved among virtually all multi-cellular organisms. In many cases apoptosis may be a default program that must be actively inhibited in healthy surviving cells. Cell death by apoptotic processes comes along with an early manifestation of membrane asymmetry which is detected as appearance of phosphatidylserine on the outer leaflet of the plasma membrane, preceding DNA fragmentation, plasma membrane blebbing and the loss of membrane integrity. Normally, granulocytes are short-lived cells with a half-life of only six to twenty hours in circulation undergoing apoptosis subsequently. The decision by a cell to submit to apoptosis is influenced by a variety of regulatory stimuli and environmental factors. Both pro-apoptotic and anti-apoptotic agents alter the lifespan of granulocytes. It is known that physiological activators of apoptosis include tumor necrosis factor (TNF), Fas ligand (FasL), transforming growth factor A, the neurotransmitters glutamate, dopamine, N-methyl-D-aspartate, withdrawal of growth factors, loss of matrix attachment, calcium and glycocorticoids. Damage-related inducers of apoptosis include heat shock, viral infection, bacterial toxins, the oncogenes myc, rel and E1A, tumor suppressor p53, cytolytic T-cells, oxidants, free radicals and nutrient deprivation. Furthermore, therapy-associated apoptosis inducers are known including gamma radiation, UV radiation and a variety of chemotherapeutic drugs, such as cisplatin, doxorubicin, bleomycin, methotrexate and vincristine. In particular, FasL and staurosporine are potent inducers of apoptosis in granulocytes. Contrary, pro-inflammatory cytokines, e.g. GM-CSF, G-CSF and IL-6, can increase the number of polymorphonuclear granulocytes (PMN) by prolonging their lifespan. Membrane-anchored proteins like PECAM-1 are also described to regulate apoptosis in granulocytes. It is a disadvantage of all mentioned inducers that they affect diverse cell types, thereby preventing the selective targeting of cells.

It was shown that molecules of the carcinoembryonic antigen (CEA) family regulate distinct cellular processes. WO 01/013937 A1 discloses peptides which are capable of modulating several cell functions by docking to CEACAM proteins, such as proliferation, differentiation, adhesion, cell activation and blocking. In detail, the peptides are directed to immune cells, e.g. leukocytes and their subtype of neutrophils. The peptides could be used as antibacterial, anti-inflammatory or anti-neoplastic agents for treating matching diseases. However, the agents are neither able to distinguish between single members of the CEA family nor to exert an influence on a specific cell activity, such as apoptosis. The treatment of mammals with these peptides is accompanied by severe adverse effects. Further specific peptides to the same CEA family target and for the same purpose are claimed in WO 2002/068601 A2. They can additionally alter an immune response which is to be specified yet.

WO 03/002764 A2 teaches a method which allows to identify therapeutically useful compounds by detecting the expression of glycoprotein antigens of the CEACAM family. The compounds can be applied in tumor prevention by increasing the sensitivity of cells to apoptosis which is controlled via gene expression. The loss of carcinoembryonic antigen-related cell adhesion molecule 1 (CEACAM1) expression is associated with the loss of apoptosis and vice versa. Therefore, pharmaceutical agents mainly affect growing cells or other expressing cells whereas medical indications involving resting cells are excluded. Available CEACAM8 is not a target. Furthermore, the transmembrane bound glycoprotein CEACAM1 is abundantly expressed in epithelia, vessel endothelia and leukocytes, there mediating a variety of cell processes, such as proliferation, cell migration, tumor growth and angiogenesis. Pre-assigned adverse effects are of disadvantage and enhanced once more by the docking ability of the compounds to other members of the CEA family, particularly to CEACAM7.

It has been recently shown by Singer et al. (2005) Eur. J. Immunol. 35 (6), 1949-1959, that CEACAM1 triggers the delay of spontaneous and FasL-induced apoptosis in rat granulocytes. That means the ligand binding to CEACAM1 prolongs the lifespan and consequently the functional capacity of granulocytes during an inflammatory reaction. The publication does not provide a tool to prevent a persistent immune response which is especially undesired in autoimmune diseases.

Autoimmune diseases concern an exaggerated immune reaction directed against the body's tissue which is aberrantly assigned as deleterious target. Severe inflammations are caused by autoimmune diseases which finally result in the damage of the affected organs. Common autoimmune diseases include autoimmune hepatitis, chronic gastritis, diabetes mellitus type 1, Morbus Crohn, Multiple Sclerosis, arthritis, psoriasis or rheumatism. Several therapeutic treatments are applied which success has to be evaluated in each case. An abatement of symptoms and a reduction of acute attacks are achieved by cortisone. However, cortisone treatment is associated with a couple of adverse effects restricting its administration to a short period. Furthermore, the weakening of the immune system is known by immune suppressive agents. For instance, methotrexate is used to treat Multiple Sclerosis or rheumatism. Changes in hemogram, gastrointestinal dysfunction, nausea, diarrhea, tumor induction, alopecia and weight reduction arising from methotrexate administration are of disadvantage.

US 2004/0185053 A1 teaches an immunoconjugate for treating autoimmune diseases, for example, which conjugate comprises a targeting moiety, a chemotherapeutic moiety and a linker binding each other. Among others, the immunoconjugate exploits the occurrence of CD66b on the surface of abnormal cells for drug targeting by antibodies. The targeting moiety and therapeutic moiety are clearly distinguished and inevitably associated. The document only addresses the question of developing novel linkers, but utilizes drugs known in prior art and having such adverse effects as already discussed.

Therefore, the technical problem forming the basis of the present invention is to provide further substances for the treatment of human autoimmune diseases, especially such substances which improve the efficacy and minimize adverse effects.

SUMMARY OF THE INVENTION

The present invention solves this problem by the use of substances being specific to CEACAM8 for the production of a medicament for the prophylactic or therapeutic treatment of human autoimmune diseases and/or gout.

Surprisingly, it has been found that CEACAM8 triggers the induction of apoptosis in cells which are able to express CEACAM8. The signal transduction is initiated by the binding of specific substances to CEACAM8.

CEACAM8 is a glycosylphosphatidylinositol-anchored membrane glycoprotein with a molecular weight of around 95 kDa. It is a member of the CEA family and a product of the CGM6 (NCA-W272) gene. CEACAM8 is present on the surface of granulocytes as well as stored in the secondary granules of granulocytes. Upon activation, CEACAM8 can be translocated from the storage pools to the plasma membrane. In addition, a soluble form is released extracellularly after stimulation. So far, no precise physiological function could be assigned to CEACAM8. It is only known that the molecule is capable of heterophilic adhesion to the closely related CEACAM1 and CEACAM6 in-vitro indicating any interaction between granulocytes or other CEACAM-expressing cells. It is also described that CEACAM8 regulates the adhesion activity of CD11/CD18 in neutrophils.

The inventor has demonstrated the unexpected effect of CEACAM8 to mediate apoptosis. It is directed against human polymorphonuclear granulocytes (PMN) consisting of approximately 90% neutrophils, approximately 2-3% basophils and approximately 6-7% eosinophils. It is of special benefit for the anti-inflammatory use of the substances that CEACAM8 is exclusively expressed in human granulocytes. The application of pro-apoptotic substances which are specific to CEACAM8 enables the specific removal of granulocytes. Other CEA family members, namely CEACAM1, CEACAM3 and CEACAM6, which are also expressed in human granulocytes, are favorably not affected.

The substances being specific to CEACAM8 are used for the manufacture of a medicament for the prophylactic or therapeutic treatment of human autoimmune diseases and/or gout. Preferably, they are used for the therapeutic treatment. A therapeutically relevant effect relieves to some extent one or more symptoms of an autoimmune disease and/or acute gout attack or returns to normality, either partially or completely, one or more physiological or biochemical parameters associated with or causative of the disease or pathological conditions. Monitoring is considered as a kind of treatment provided that the substances are administered in distinct intervals, e.g. in order to booster the apoptosis response and eradicate the symptoms of the disease completely. Either the identical substance or different substances can be applied. In the meaning of the invention, prophylactic treatment is only advisable against acute gout attacks or if the subject possesses any preconditions for the outbreak of an autoimmune disease, such as a familial disposition, a genetic defect or a previously passed disease. As used herein, including the appended claims, plural forms of words include their corresponding singular referents, such as "a," "an," and "the" unless the context clearly dictates otherwise. Thus, e.g., reference to "substances" includes one substance or more different substances.

In an embodiment of the present invention, the substances being specific to CEACAM8 are used for the production of a medicament for the prophylactic or therapeutic treatment of arthritis, arthrosis, autoimmune hepatitis, chronic gastritis, colitis, such as colitis ulcerosa, diabetes mellitus type 1, Morbus Crohn, Multiple Sclerosis, neurodermatitis, pancreatitis, psoriasis and/or rheumatism, preferably arthritis, arthrosis, chronic gastritis, Morbus Crohn, neurodermitis, pancreatits, rheumatism and/or psoriasis, more preferably arthritis, arthrosis, rheumatism and/or psoriasis, most preferably arthrosis, rheumatism and/or psoriasis.

The term "specific substances" as used herein comprises molecules with high affinity to CEACAM8 or variants thereof in order to ensure a reliable binding. The degree of variation between native CEACAM8 and its variants is inevitably limited by the requirement of recognition by the specific substances. Preferably, the homology amounts to at least 85%. Possible alterations comprise deletion, insertion, substitution, modification and addition of at least one amino acid, or the fusion with another protein. However, the binding site on the antigen CEACAM8 which is recognized by a specific substance can be a definite small region, such as an epitope to be bound by an antibody. Such a region can be either used as isolated molecule or inserted into other proteins than CEACAM8 to induce apoptosis. Particularly, the specific epitope of CEACAM8 which is recognized by the monoclonal antibody mAb 80H3 is sufficient for the induction of apoptosis. These regions and epitopes, respectively, are also included in CEACAM8 variants which are a target of CEACAM8-specific substances in the meaning of the invention. CEACAM8-specific substances comprise nucleic acids, peptides, proteins, carbohydrates, polymers and small molecules having a molecular weight between 50 and 1,000 Da. The proteins or peptides are preferably selected from the group consisting of antibodies, cytokines, lipocalins, receptors, lectins, avidins, lipoproteins, glycoproteins, oligopeptides, peptide ligands and peptide hormones. The nucleic acids are preferably single or double stranded DNA or RNA, oligonucleotides, aptamers or Spiegelmers, or parts thereof. Preferred examples of low molecular weight ligands are steroids.

In a preferred embodiment of the invention, lipocalins are used. Lipocalins are a widespread group of small and robust proteins that are usually involved in the physiological transport or storage of chemically sensitive or insoluble compounds. Despite low mutual sequence homology, lipocalins share a structurally conserved β-barrel, supporting four loops at one end, which form the entrance to a binding pocket. The protein architecture is reminiscent of immunoglobulins with hyper-variable loops on top of a rigid framework. The binding site can be reshaped in order to recognize prescribed target molecules of different shape with high affinity and specificity. So-called engineered ANTICALINS recognize hapten-like compounds, peptides and protein targets, e.g. extracellular domains of cell surface receptors. Lipocalins and derivatives thereof are composed of a single polypeptide chain with 160 to 180 amino acid residues, being just marginally bigger than a single immunoglobulin domain. ANTICALINS are simply produced by secretion from *E. coli* or yeast and possess a high thermal stability. In addition, fusion proteins with enzymes as well as bi-specific binding proteins (DUOCALINS) can be prepared.

In another preferred embodiment of the invention, antibodies are used. Antibody denotes a polypeptide essentially encoded by an immunoglobulin gene or fragments thereof. According to the invention, antibodies are present as intact immunoglobulins or a number of well-characterized fragments.

There is a distinct number of specific antibodies against CEACAM8 existing. In a preferred embodiment, the specific substances are represented by anti-CEACAM8 antibodies which are described in the art. Polyclonal antibodies are usually produced in mammal organisms when an immune response is caused by antigens being strange to the organism and having a molecular weight which exceeds 3.000 g/mol. A preferred polyclonal antibody to be used as substance in the meaning of the present invention is Polyclonal Rabbit anti-human Carcinoembryonic Antigen which is commercially available at DakoCytomation (Glostrup, Denmark). Popular techniques for producing monoclonal antibodies, such as the hybridoma technology, are also well-known to the skilled artisan. Favorable host species for antibody production comprise rat, goat, rabbit, bunny and mouse. In detail, both polyclonal and monoclonal antibodies are known which are directed to the human CEACAM8 antigen. Further polyclonal and monoclonal antibodies can be selected against CEACAM8 and fragments thereof. Preferably, monoclonal antibodies directed against CEACAM8 are applied as specific substances in the present invention.

Antibody fragments are preferably selected from the group consisting of Fab fragments, F(ab')$_2$ fragments, single chain antibodies (scFv), variable regions, constant regions, H chain ($V_H$) and L chain ($V_L$), more preferably Fab fragments, F(ab')$_2$ fragments and scFv. It is well-known that only a small portion of an antibody molecule, the paratope, is involved in the binding of the antibody to its epitope. The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain ($V_L$) and a portion of the antibody heavy chain denoted Fd. The Fd fragments are the major determinant of antibody specificity and retain epitope-binding ability in isolation. Within the antigen-binding portion of an antibody, there are complementarity determining regions (CDRs) which directly interact with the epitope of the antigen, and framework regions (FRs) which maintain the tertiary structure of the paratope. In both the heavy chain Fd fragment and the light chain of IgG immunoglobulins, there are four framework regions (FR1 through FR4) separated respectively by three complementarity determining regions (CDR1 through CDR3). The CDRs, in particular the CDR3 regions, more particularly the heavy chain CDR3, are largely responsible for antibody specificity.

Fragments, such as Fab fragments and F(ab')$_2$ fragments, can be produced by cleavage using various peptidases. Furthermore, fragments can be engineered and recombinantly expressed, preferably scFv. Thus, the invention involves polypeptides of numerous size and type that bind specifically to CEACAM8. These polypeptides may also be derived from sources other than antibody technology. For example, such polypeptide binding substances can be provided by degenerate peptide libraries which are readily prepared in solution, in immobilized form or as phage display libraries. Combinatorial libraries can also be synthesized of peptides containing one or more amino acids. Furthermore, libraries can be synthesized of peptoids and non-peptide synthetic moieties. Phage display is particularly effective in identifying binding peptides useful according to the invention. Additionally, small polypeptides including those containing the CEACAM8-binding fragment (CDR3 region) may easily be synthesized or produced by recombinant means to produce a CEACAM8-binding substance useful according to the invention. Such methods are well known to those of ordinary skill in the art. Peptides can be synthesized for example, using automated peptide synthesizers which are commercially available. The peptides can be produced by recombinant techniques comprising the incorporation of the DNA which expresses the peptide into an expression vector and the transformation of cells with the expression vector to produce the peptide.

In a more preferred embodiment of the present invention, the monoclonal antibodies are mAb 80H3, mAb B13.9, mAb B4-EA4, mAb BIRMA 17C, mAb BL-B7, mAb G10F5, mAb MF25.1, mAb 12-140-5, mAb JML-H16, mAb Kat4c, mAb TET2, mAb YG-C46A8, mAb YG-C51B9, mAb C76G4 and/or mAb YG-C94G7, preferably mAb 80H3, mAb B13.9, mAb B4-EA4, mAb BIRMA 17C, mAb BL-B7, mAb G10F5, JML-H16 and/or mAb MF25.1, more preferably mAb 80H3 and/or mAb B13.9, most preferably mAb 80H3. The code designations of the monoclonal antibodies refer to the clone name in the HLDA (human leukocyte differentiation antigens) Antibody Database. Mouse monoclonal antibodies are mAb 80H3, mAb B13.9, mAb B4-EA4, mAb BIRMA 17C, mAb BL-B7, mAb G10F5, mAb JML-H16 and mAb MF25.1. The antibody mAb 80H3 is e.g. commercially available at Immunotech, Marseilles (France), Serotec, abcam and GeneTex. The company abcam also sells the mAb BL-B7. The mAb G10F5 is e.g. provided by BD Pharmingen, BioLegend and StemCell Technologies. The antibody mAb B13.9 is e.g. distributed via immunotools.com, Caltaq and Hoelzel-Biotech. More suppliers for these antibodies as well as the other antibodies mentioned above are known to the skilled artisan.

It is to be understood that these antibodies can be used in the present invention beyond their special formulation and purpose as given by the distributor. None of the antibodies show a significant cross-reactivity or interference to other natural or recombinant human proteins, or to other natural or recombinant proteins including members of the CEA family. Thus, a strong induction of apoptosis, but less side effects especially caused via other CEACAM signal cascades are guaranteed. Preferred antibodies which interact mono-specifically with their CEACAM8 target are the mouse monoclonal antibodies mAb 80H3, mAb B4-EA4 mAb B13.9, mAb BIRMA 17C, mAb BL-B7, mAb G10F5, JML-H16 and mAb MF25.1 which can be applied as single molecules or in any combination. Prior human application, these antibodies are usually processed to antibodies which are chimeric antibodies, such as a chimeric murine/human antibody, or humanized antibodies, or they are re-produced as human antibodies.

It is well-established in the art that the non-CDR regions of a mammalian antibody including those mentioned above may be replaced with similar regions of conspecific or heterospecific antibodies while retaining the epitopic specificity of the original antibody. This is most clearly manifested in the development and use of humanized antibodies in which non-human CDRs are covalently joined to human FR and/or Fc/pFc' regions to produce a functional antibody. Such antibodies, including fragments of intact antibodies with antigen-binding ability, are often referred to as chimeric antibodies. Thus, as will be apparent to one of ordinary skill in the art, the present invention also provides for chimeric antibodies in which the Fe and/or FR and/or CDR1 and/or CDR2 and/or light chain CDR3 regions have been replaced by homologous human or non-human sequences, for chimeric F(ab')$_2$ fragment antibodies in which the FR and/or CDR1 and/or CDR2 and/or light chain CDR3 regions have been replaced by homologous human or non-human sequences, for chimeric Fab fragment antibodies in which the FR and/or CDR1 and/or CDR2 and/or light chain CDR3 regions have been replaced by homologous human or non-human sequences, and for chimeric Fd fragment antibodies in which the FR and/or CDR1 and/or CDR2 regions have been replaced by homologous human or non-human sequences.

Preferred nucleic acids to be used as CEACAM8-specific substances in the present invention are DNA aptamers and RNA aptamers which have been found to express a high affinity for a wide variety of molecules called targets. More preferred are RNA aptamers since the 2'-hydroxyl group available in RNA promotes a couple of intra- and intermolecular contacts, the latter being between molecules of the same sequence, different sequences, or between RNA and any other molecule which is not composed of RNA. These nucleic acid ligands can be identified by an efficient in-vitro selection procedure—the so-called SELEX process (systematic evolution of ligands by exponential enrichment). Since RNA is very susceptible to nucleolytic degradation in biological solutions, RNA aptamers should be chemically modified using phosphorothioates, locked nucleic acids, or Spiegelmers, for instance. L-RNA versions of aptamers called Spiegelmers are especially long-lived as they are essentially impervious to natural degradation processes. The aptamers can be synthesized using standard phosphoramidite chemistry. In addition, RNA aptamers having more than approximately 30 nucleotides can be favorably synthesized in large amounts by in-vitro transcription. Selection, synthesis, and purification of aptamers are well-known to those skilled in the art.

In another embodiment of the present invention, substances being mono-specific to CEACAM8 are used for the production of a medicament for the prophylactic or therapeutic treatment of human autoimmune diseases and/or gout. The term "mono-specific" denotes a mode of binding which is characterized by the exclusive recognition of a single target. The mono-specific substances used in the present invention only recognize the CEACAM8 target or variants thereof. The receptor/ligand-interaction is featured by high affinity, high selectivity and minimal or even none cross-reactivity to other target molecules, particularly other CEACAMs. Unhealthy and harmful impacts on other cell types bearing other CEACAMs are advantageously overcome by the mono-specific binding to CEACAM8. For instance, CEACAM8-specific substances do not interfere with epithelia, endothelia, dendritic cells, NK cells, monocytes, macrophages, B-lymphocytes or T-lymphocytes.

Preferred mono-specific substances of the present invention are the monoclonal antibody mAb 80H3 and/or the monoclonal antibody mAb B13.9. The mAb 80H3 and mAb B13.9 are known to bind specifically to CEACAM8 but not to any other CEACAMs.

The substances being specific to CEACAM8 are adapted in forms which are suitable for oral administration, such as tablets, film tablets, lozenges, capsules, pills, powders, solutions, dispersions, suspensions or depot forms thereof, for transdermal administration, such as solutions, suspensions, creams, ointments, gels, emulsions or band-aids, for parental administration, such as suppositories, and for intravenous infusion, subcutaneous injection or intramuscular administration, examples for the latter three are solutions and suspensions. The substances can also be adapted for topical, transmucosal, transurethal, vaginal, rectal or pulmonary administration in the appropriate formulations given above.

The formulations are produced in a known way using common solid or liquid carriers, diluents and/or additives and usual adjuvants for pharmaceutical engineering and with an appropriate dosage depending on the intended mode of application. These pharmaceutically acceptable excipients comprise salts, buffers, fillers, chelating agents, antioxidants, solvents, bonding agents, lubricants, tablet coatings, flavor additives, flavors, preservatives and suspending agents. In the meaning of the invention, an adjuvant denotes every substance which enables, intensifies or modifies a specific immune response against the CEACAM8-specific substances if administered simultaneously, contemporarily or sequentially. Known adjuvants for injection solutions are for example aluminum compositions, such as aluminum hydroxide or aluminum phosphate, saponins, such as QS21, muramyldipeptide or muramyltripeptide, proteins, such as gamma-interferon or TNF, M59, squalen or polyols. The amount of excipient material that is combined with the active substance to produce a single dosage form varies depending upon the host treated and the particular mode of administration.

In a preferred embodiment of the invention, the formulation to be administered is an injection solution which means a therapeutic or prophylactic use of the medicament for treating autoimmune diseases and/or gout. The initial effect can be boostered by subsequent injections. Furthermore, the inoculation can be administered before or following an outbreak of the disease once or several times, thereby acting as therapy. The forms or methods for manufacturing injection solutions according to the present invention are not particularly limited, and a composition in a desired form can be prepared by applying a single method available in the field of the art or methods in an appropriate combination. Aqueous media, such as distilled water and physiological saline, as well as one or more kinds of pharmaceutical additives available in the field of the art can be used for the manufacture of an injection solution. For example, buffering agents, pH adjusting agents, solubilizing aids, stabilizing agents, soothing agents, antiseptics, and the like can be used, and specific ingredients thereof are well known to those skilled in the art. The composition can also be provided as a solid preparation such as a lyophilized preparation, and then prepared as an injection by adding a solubilizing agent, such as distilled water, for injection before use.

Depending upon the manner of introduction, the compounds may be formulated in a variety of ways as discussed below. The concentration of therapeutically active substances in the formulation may vary from about 0.1 to 100 wt %. The solution may be administered alone or in combination with other treatments. In a preferred embodiment, the substances to be injected are in a water-soluble form, such as a pharmaceutically acceptable salt, which is meant to include both acid and base addition salts. The injection solution may also include one or more of the following: carrier proteins, such as serum albumin, buffers, stabilizing agents, coloring agents, and the like. Additives are well known in the art, and they are used in a variety of formulations.

For instance, the substances can be injected into the knee of a patient suffering from a persistent trauma.

Alternatively, a knee injury, even a cold or another sickness represents a stimulating event which can be exploited to treat any autoimmune diseases in the meaning of the present invention. It is known that PMNs are initially primed by injury and acute inflammations. The inventor has surprisingly found that pre-primed PMNs are especially susceptible to undergo apoptosis after treatment with the substances which are specific to CEACAM8.

It will be understood that the specific dose level, frequency and period of administration of any particular human subject will depend upon a variety of factors including the activity of the specific substance employed, the subject's age, body weight, general health, sex, diet time of administration, route of administration, rate of excretion, drug combination and the severity of the specific therapy. They can be determined by one of skill in the art as a matter of routine experimentation. Modulating apoptosis, i.e. inducing it, is sufficient to produce the desired effect in which the symptoms associated with the conditions characterized by aberrant granulocytes activity are ameliorated or decreased. In an embodiment of the present invention the substances are adapted for an administration in a dose rate of 0.01 mg to 2 g per kilogram of body weight and per day. Less than 1 mg per kilogram of body weight and per day are administered for low dose treatments, preferably less than 0.1 mg. Contrary, at least 50 mg per kilogram of body weight and per day are administered for high dose treatments, preferably 50 mg to 200 mg. Such a treatment can be applied for four weeks and subsequently reduced to lower dose rates, such as 10 to 15 mg. Extremely higher dose rate of up to 1 g per kilogram of body weight twice a day are applicable. Usually, dose rates of 20 to 60 mg per kilogram of body weight and per day are administered.

Object of the present invention is also a pharmaceutical composition comprising as active substance one or more substances selected from the group consisting of the monoclonal antibodies mAb 80H3, mAb B13.9, mAb B4-EA4, mAb BIRMA 17C, mAb BL-B7, mAb G10F5, mAb MF25.1, mAb 12-140-5, mAb JML-H16, mAb Kat4c, mAb TET2, mAb YG-C46A8, mAb YG-C51B9, mAb C76G4 and mAb YG-C94G7, more preferably mAb 80H3, mAb B13.9, mAb B4-EA4, mAb BIRMA 17C, mAb BL-B7, mAb G10F5 and/or mAb MF25.1, most preferably mAb 80H3 and/or mAb B13.9.

Another object of the present invention is a method for screening substances which induce apoptosis comprising the steps of:
  providing a cell sample being capable of expressing CEACAM8,
  dividing the sample into portions,
  incubating at least one portion with substances being screened,
  comparing the apoptosis rate in these portions with portions which are not incubated with these substances, and
  detecting the specific binding of substances to CEACAM8 inducing apoptosis.

The inventive method makes the identification of substances possible which exert an influence on the signal cascade via CEACAM8 and increase the apoptosis rate of cells. The cell sample refers to primary cells or genetically engineered cells. The latter are capable of expressing CEACAM8 by transfection with appropriate vectors harboring the CGM6 (NCA-W272) gene or parts thereof. Preferably, the recombinant cells are of eukaryotic origin. The primary cells are human granulocytes which are preferred in the method of the invention. The human granulocytes can also be established as cell line. Furthermore, cell homogenates or tissue extracts containing CEACAM8-expressing cells can be used. The cell sample is divided into multiple portions. At least two portions are provided; one is used for screening while the other one serves as negative control. Preferably, the number of portions for screening exceeds the number of control portions. Usually, numerous portions are subjected to a high-throughput screening.

The substances to be screened in the inventive method are not restricted anyway. In an embodiment of the invention, the substances are selected from the group of nucleic acids, peptides, carbohydrates, polymers, small molecules having a molecular weight between 50 and 1,000 Da, and proteins, preferably antibodies, cytokines and lipocalins. In a preferred embodiment of the present invention, the substances are monoclonal antibodies, preferably mAb 80H3, mAb B13.9, mAb B4-EA4, mAb BIRMA 17C, mAb BL-B7, mAb G10F5, mAb MF25.1, mAb 12-140-5, mAb JML-H16, mAb Kat4c, mAb TET2, mAb YG-C46A8, mAb YG-C51 B9, mAb C76G4 and/or mAb YG-C94G7, more preferably mAb 80H3, mAb B13.9, mAb B4-EA4, mAb BIRMA 17C, mAb BL-B7, mAb G10F5 and/or mAb MF25.1, most preferably mAb 80H3 and/or mAb B13.9. In another preferred embodiment of the invention, the substances are polyclonal antibodies, preferably Polyclonal Rabbit anti-human Carcinoembryonic Antigen. The prior teaching of the present specification concerning the use of CEACAM8-specific substances for the production of a medicament for the prophylactic or therapeutic treatment of human autoimmune diseases is considered as valid and applicable without restrictions to the method for screening such substances which induce apoptosis if expedient.

The substances are often available in libraries. It is preferred to incubate a single substance within a distinct portion of the cell sample. However, it is also possible to investigate the cooperative effect of substances by incubating at least two substances within one portion. A further portion of cells which are susceptible to apoptosis is simultaneously incubated in the absence of the substances. The incubation process of cells depends on various parameters, e.g. the cell type and the sensitivity of detection, which optimization follows routine procedures known to those skilled in the art.

The identification of effective substance in the meaning of the invention is directly performed by determining the apoptosis rate or the rate constant of apoptosis kinetics, respectively. Therefore, the number of apoptotic cells or the number of viable cells, respectively, is measured at a particular time. Common methods of the art comprise staining with annexin V and/or propidium iodide, or the measurement of nucleosomes released during apoptosis by means of a sandwich ELISA. Another method records immunochemically the caspase-induced proteolysis of cytokeratins and the produced neo-epitopes of this filamentous protein. The measured values are related to the cell number at the beginning of the experiment and to the period of induction. The higher the number of apoptotic cells after a certain period, the higher is the initial apoptosis rate or the rate constant, respectively. The calculated apoptosis rates, constants or just apoptotic cell numbers of the substance-incubated portions are compared with the negative control. A substance which induces apoptosis is indicated by any value exceeding the corresponding value of the negative control.

Among those substances being revealed to induce apoptosis each or some representatives are selected for further analysis. Preferably, the substances showing the greatest discrepancy to the control are chosen. They are analyzed for specificity to CEACAM8 to exclude another signal transduction which is not initiated by CEACAM receptor binding, and additionally tested for such a cross-reactivity which may promote apoptosis by linked pathways if simultaneous docking to further receptors occurs. Accepting of any cross-reactivity has to be assessed with regard to other functions of the co-recognized receptors which interference is to be avoided in the meaning of the present invention. Several methods are known in the field of the art for detecting specific and/or mono-specific binding, such as gel shift experiments, Biacore measurements, X-ray structure analysis, competitive binding studies, and the like. In a preferred embodiment of the present invention, the mono-specific binding to CEACAM8 of substances inducing apoptosis is detected.

Alternatively, cells which are not able of expressing CEACAM8 can serve as negative control which is subjected to the substances. In this way apoptosis cannot inevitably be affected via CEACAM8. Any increased susceptibility to apoptosis in the negative control is caused by another pathway than that the present invention is based on. It is required that the different cell types which are used either for screening or as control show a comparable half-life and apoptosis behavior, the latter being characterized by similar features of the apoptotic cells which should be favorably detected by the same method. CEACAM8-defective cells can be originated from primary cells, cell lines, recombinant cells, cell homogenates and tissue extracts. For example, rat granulocytes or CEACAM8 deletion mutants of human granulocytes are used as negative control. Deletion mutants of natural origin can be obtained from patients suffering from paroxysmal nocturnal hemoglobinuria (PNH) whose cells are lacking GPI-anchored proteins including CEACAM8. This modified method requires an equal number of trials for actual screening and for the control experiment, i.e. each substance is incubated at least twice. The double number of trials is compensated by assessing the apoptosis susceptibility and the substance specificity to CEACAM8 in parallel. The assessment is performed by correlating the apoptosis in the parallel trials with the apoptosis in a portion of CEACAM8-defective cells which is incubated in the absence of substances (so called negative control of the negative control). That means the CEACAM8-defective cells are necessarily divided into multiple portions in advance. Desired substances in the meaning of the invention are indicated by any higher level of apoptotic cells in the CEACAM8-expressing cell portion compared with both levels of apoptotic cells in the CEACAM8-defective cell portions which are incubated either with substances or not, whereby the latter levels in the portions of CEACAM8-defective cells have to be equivalent.

The present invention also relates to a method for inducing apoptosis in human granulocytes, wherein a human sample comprising the granulocytes is incubated with at least one substance being specific to CEACAM8 and specific incubation products are formed, thereby inducing apoptosis. The sample is withdrawn from a human to be examined following good medical practice. In the present invention, the sample preferably consists of blood, serum, plasma, saliva or urine. It is also possible to gather a tissue sample by biopsy. The sample may be purified to remove disturbing substances, such as inhibitors for the formation of hydrogen bonds, or the granulocytes can be concentrated in the sample. Downstream-processing and/or concentrating is performed by routine techniques, such as centrifugation or gel filtration. It is recommended to combine several methods for better yields. The human sample is stored, such as frozen, cultivated for a certain period or immediately incubated with substances which are specific to CEACAM8 or variants thereof. Incubation denotes the contacting of specific substances with CEACAM8 which can be realized without a chemical conversion, e.g. antibody-CEACAM8 binding, or may involve a biochemical reaction, e.g. by an enzyme-CEACAM8 complex. The accessibility of granulocytes and/or CEACAM8 in the sample can be improved by adding chemical solutions and/or applying physical procedures, e.g. impact of heat. Cultivation and incubation of granulocytes are known to those skilled in the art following standard procedures. As result of the incubation, specific incubation products comprising substance-CEACAM8-complexes are formed. The apoptotic processes which are induced can be monitored by the techniques already described in the course of the present specification. This in-vitro method is preferably applied to samples of humans suffering from an autoimmune disease. Testing of several specific substances makes the selection of that substance possible which is best suited for the treatment of the human subject. Preferably, a mono-specific substance is selected. The in-vivo dose rate of the chosen substance is advantageously pre-adjusted to the apoptosis susceptibility of the specific granulocytes with regard to their in-vitro data. Therefore, the therapeutic efficacy is remarkably enhanced.

It is still another object of the invention to use substances being specific to CEACAM8 for the induction of apoptosis in human granulocytes in-vitro. In an embodiment of the invention, the substances are selected from the group of nucleic acids, peptides, carbohydrates, polymers, small molecules having a molecular weight between 50 and 1,000 Da, and proteins, preferably antibodies, cytokines and lipocalins. The prior teaching of the present specification concerning the use of CEACAM8-specific substances for the production of a medicament for the prophylactic or therapeutic treatment of human autoimmune diseases is considered as valid and applicable without restrictions to the in-vitro use of such substances for apoptosis induction if expedient.

Another preferred object of the present invention relates to the use of monoclonal antibodies as substances which are specific to CEACAM8, preferably mAb 80H3, mAb B13.9, mAb B4-EA4, mAb BIRMA 17C, mAb BL-B7, mAb G10F5, mAb MF25.1, mAb 12-140-5, mAb JML-H16, mAb Kat4c, mAb TET2, mAb YG-C46A8, mAb YG-C51B9, mAb C76G4 and/or mAb YG-C94G7, more preferably mAb 80H3, mAb B13.9, mAb B4-EA4, mAb BIRMA 17C, mAb BL-B7, mAb G10F5 and/or mAb MF25.1, most preferably mAb 80H3 and/or mAb B13.9. The monoclonal antibody mAb 80H3 and/or the monoclonal antibody mAb B13.9 are used in an active concentration of 0.1 to 1000 µg/ml, more preferably in an active concentration of 5 to 200 µg/ml, most preferably in an active concentration of 25 to 35 µg/ml. In particular, the active concentrations specified above are applied in samples having $10^5$ to $10^9$ granulocytes/ml, more preferably $5*10^6$ to $5*10^7$ granulocytes/ml. Herein, active concentration refers to the final antibody concentration which is present after mixing the antibody with the sample of human granulocytes and optionally further components. The antibody is supplied in a stock solution having a higher concentration than the active concentration.

Still another preferred object of the present invention relates to the use of polyclonal antibodies as substances which are specific to CEACAM8, preferably Polyclonal Rabbit anti-human Carcinoembryonic Antigen.

After using substances being specific to CEACAM8 for induction of apoptosis in-vitro, at least 50% of human granulocytes are apoptotic following five hours of incubation, preferably at least 70% of granulocytes, more preferably at least 90% of granulocytes. Comparative trials lacking specific substances to CEACAM8 result in approximately 40% of cells which have naturally undergone apoptosis. All trials are incubated under identical conditions with the exception of substance supplement. Preferably, an active concentration of the mono-specific antibodies mAb 80H3 and/or mAb B13.9, and a number of granulocytes are used as stated above. Further details of the material and experimental procedure are given in the examples which are especially preferred. The substances are of particular efficacy in inducing apoptosis if pre-stimulated granulocytes are used. For example, the in-vitro preparation of granulocytes can be performed by the granulocyte-macrophage colony stimulating factor (GM-CSF), G-CSF, lipopolysaccharide (LPS), IL-8 or any combination thereof.

The present invention also relates to a method for treating gout and/or a human autoimmune disease, preferably arthritis, arthrosis, rheumatism and/or psoriasis, wherein an effective amount of at least one substance being specific to CEACAM8 is administered to a human in need of such treatment. The prior teaching of the present invention and embodiments thereof is considered as valid and applicable without restrictions to the method of treatment if expedient.

DETAILED DESCRIPTION OF THE PRESENTLY PREFERRED EMBODIMENTS

The following examples are provided by way of illustration and not by way of limitation. Within the examples, standard reagents and buffers that are free from contaminating activities (whenever practical) are used.

EXAMPLE 1

Materials were obtained from Sigma (Taufkirchen, Germany) unless stated otherwise. Complete culture medium consisted of RPMI 1640 (Gibco-Life Technology, Eggenstein, Germany) supplemented with 2 mM L-glutamine (Gibco), 100 U/ml penicillin (Gibco), 100 µg/ml streptomycin (Gibco) and 10% heat-inactivated FCS (Gibco). The mouse monoclonal antibody binding to CEACAM1 (4/3/17) and the monoclonal antibody binding to CEACAM6 (mAb 13H10) were a gift of F. Grunert (Institute for Immunobiology, Freiburg, Germany). The mouse monoclonal antibody binding to CEACAM3 (mAb F4-82) was obtained from Motomu Kuroki, School of Medicine, Fukuoka, Japan. The mouse monoclonal antibody binding to CEACAM8 (mAb 80H3) was obtained from Immunotech, Marseilles, France.

Granulocytes were isolated from heparinized (5 U/ml) peripheral blood of rats, healthy donors and patients with a severe knee injury. After erythrocyte sedimentation through Plasmasteril® (Fresenius, Bad Homburg, Germany), PMNs and PBMCs of the leukocyte-rich plasma were separated by gradient centrifugation via Ficoll-Paque™ (Amersham). The remaining erythrocytes in the pelleted fractions were lysed by repeated suspension in cold 0.2% NaCl solution for 20 seconds followed by washing with cold PBS. More than 96% of the remaining cells were granulocytes as judged by morphological criteria and FACScan™ analysis using a specific differentiation marker for PMN. Cell viability was >97% as determined by trypan blue staining.

Granulocytes were resuspended in RPMI medium at a final concentration of 100,000 cells in a final volume of 100 µl. The cells were then incubated at 37° C. for 5 to 6 hours with or without mouse monoclonal antibodies (30 µg/ml) as indicated. In detail, granulocytes were cultured with control 1 g, anti-CEACAM1 mAb 4/3/17, anti-CEACAM3 mAb F4-82, anti-CEACAM6 mAb 13H10 and anti-CEACAM8 mAb 80H3.

Figure 4:
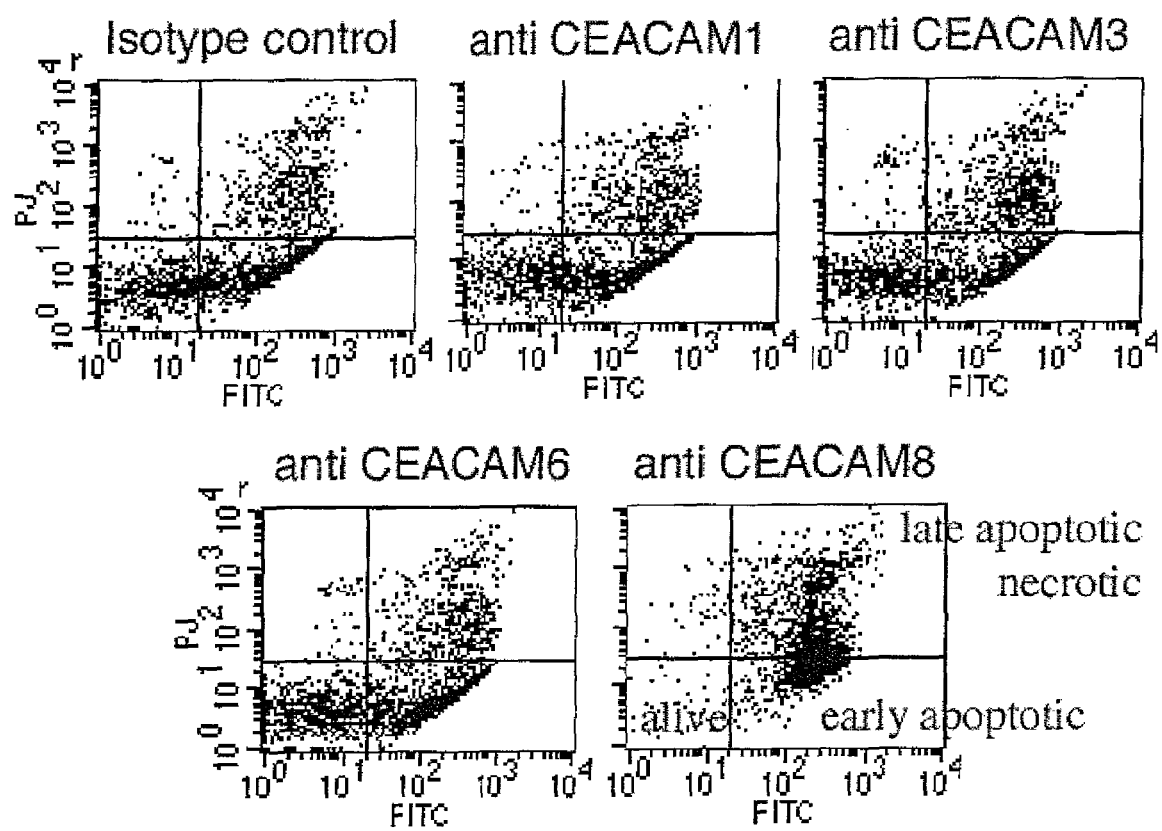
FIG. 4 shows the induction of apoptosis triggered by CEACAM8 in human granulocytes of injured donors. The percentage of cell survival is assessed by double-staining for FITC-annexin V/PI and flow cytometry.

A procedure based on double-staining for annexin V and propidium iodide (PI) was performed to determine and distinguish between early and late apoptotic/necrotic cells. Annexin V binds to phosphatidylserine which appears in the outer leaflet of the plasma membrane in early apoptotic cells. In late apoptotic cells, the plasma membrane becomes permeable and allows uptake of propidium iodide which intercalates into DNA. Thus, annexin V labels both early and late apoptotic cells whereas propidium iodide only labels late apoptotic and necrotic cells. Labeling with FITC-coupled annexin V and propidium iodide was performed according to the manufacturer's protocol (Bender MedSystems, Vienna, Austria). The labeled cells were analyzed by flow cytometry in a FACScan instrument and by means of CELLQuest software (BD Biosciences). As shown in FIG. 4, three populations of cells were actually observed after antibody treatment: living cells (not stained, lower left quadrants), early apoptotic cells (annexin V-positive, PI-negative, lower right quadrants) and cells in the late stage of apoptosis (annexin V-positive, PI-positive, upper right quadrants).

Figure 1:
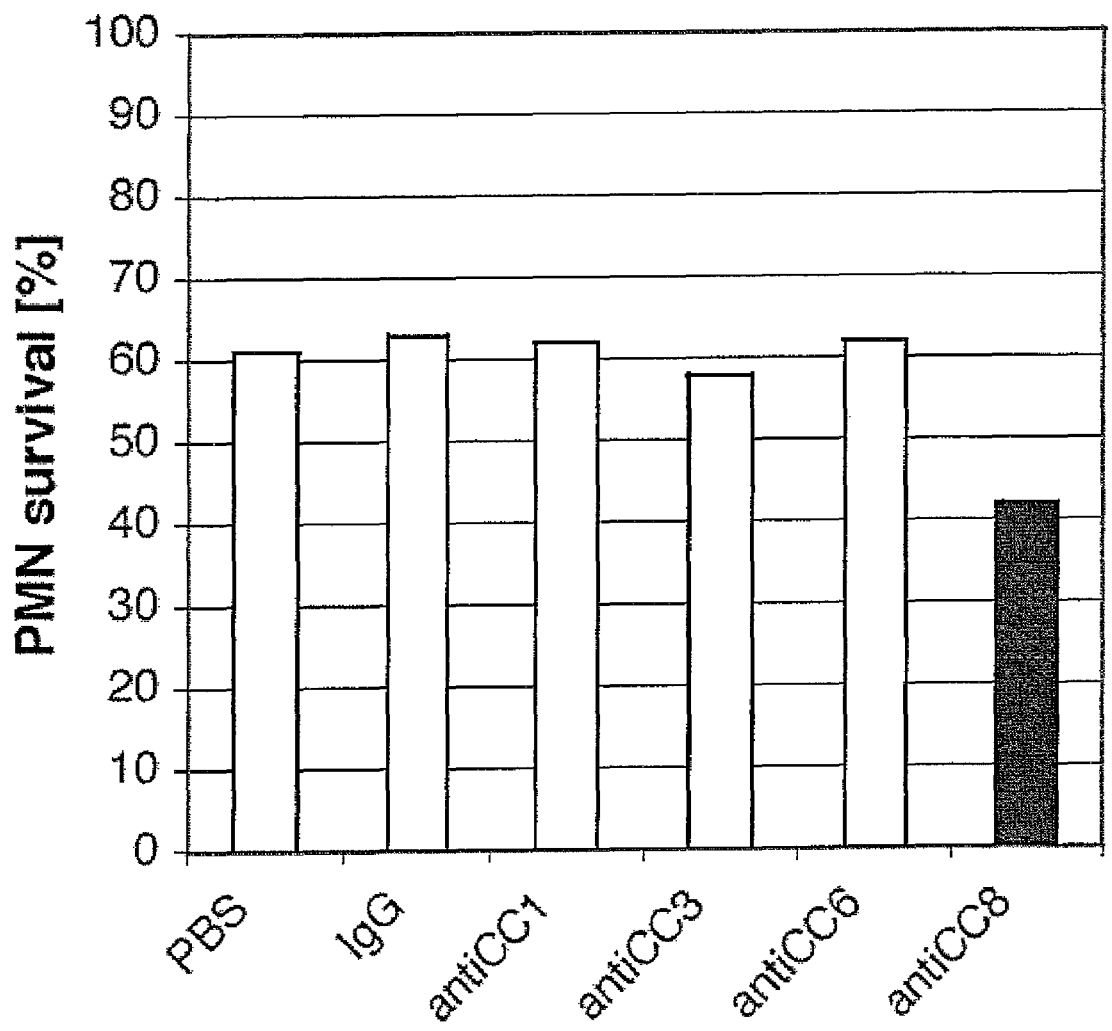
FIG. 1 shows the alteration of spontaneous apoptosis triggered by CEACAM8 in human granulocytes of healthy donors.

Apoptosis in human granulocytes isolated from healthy donors was evidently increased following incubation with the anti-CEACAM8 mAb 80H3 as shown in FIG. 1 (42% versus 63% in the control 1 g). Interestingly, the apoptosis-inducing effect of CEACAM8 in primed PMNs was even clearer (2.3% versus 21 to 27% in FIG. 4) than in PMNs isolated from healthy donors (42% versus 57 to 62% in FIG. 3). Contrary, antibodies binding to CEACAM1, CEACAM3 or CEACAM6 did not alter the percentage of surviving PMNs. Thus, CEACAM8 (but not CEACAM1, CEACAM3 and CEACAM6) mediated the induction of apoptosis in human PMNs or human granulocytes, respectively (FIG. 1 and FIG. 4). These results confirm that ligand binding to CEACAM8 which is mimicked by the monoclonal antibody 80H3 led to a dramatic induction of apoptosis in human granulocytes.

A contamination in the mAb 80H3 leading to the apoptotic effect could be ruled out. Rat granulocytes treated with mAb 80H3 did not show any alteration with respect to cell survival, therefore serving as negative control (data not shown).

EXAMPLE 2

Figure 2:
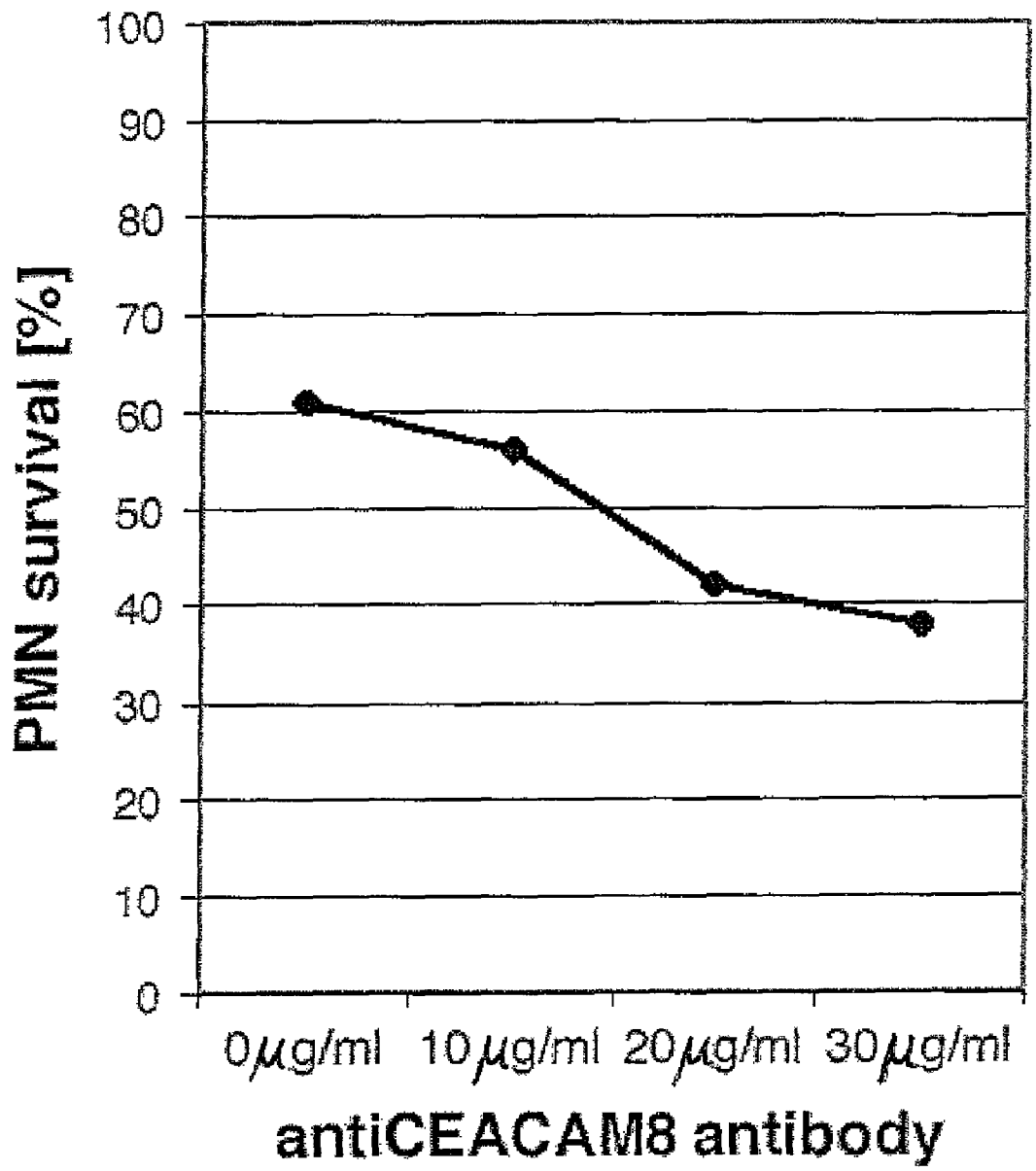
FIG. 2 shows the dose-dependence of the CEACAM8-induced apoptosis.

Granulocytes were isolated from heparinized (5 U/ml) peripheral blood of healthy donors and resuspended as described in Example 1. Subsequently, the cells were cultured for 5 hours with anti-CEACAM8 mAb 80H3 (0 µg/ml, 10 µg/ml, 20 µg/ml and 30 µg/ml). The percentage of cell survival was assessed by double-staining with FITC-annexin V/propidium iodide and flow cytometry as described in Example 1. The CEACAM8-triggered cell death in human PMNs runs in a dose-dependent manner (FIG. 2).

EXAMPLE 3

Figure 3:
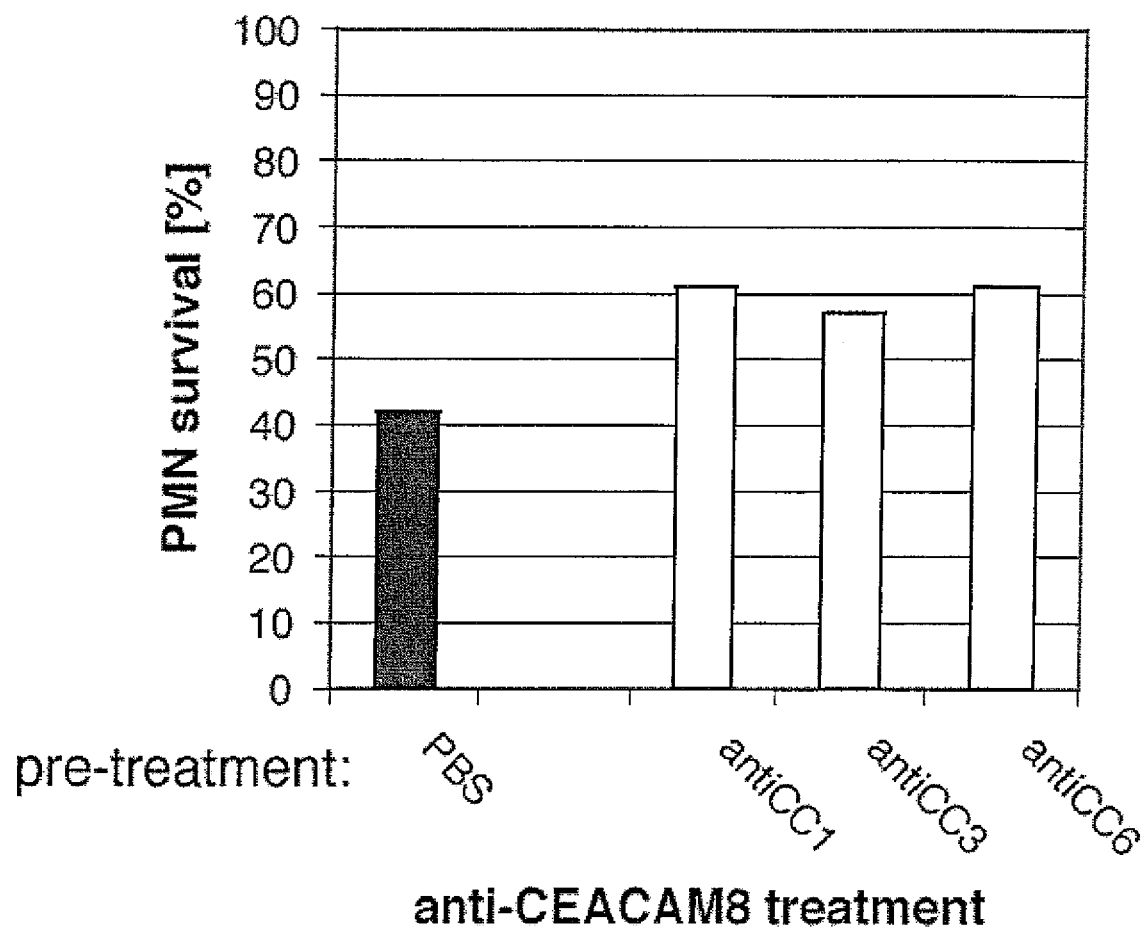
FIG. 3 shows the hindering of CEACAM8-induced apoptotic effect in human PMNs by CEACAM1, CEACAM3 and CEACAM6.

Peripheral blood granulocytes were isolated from peripheral blood of a patient with a severe knee injury and resuspended as described in Example 1. Following 10 min pre-incubation with anti-CEACAM1 mAb 4/3/17 (30 µg/ml), anti-CEACAM3 mAb F4-82 (30 µg/ml) or anti-CEACAM6 mAb 13H10 (30 µg/ml) at room temperature, granulocytes were treated with anti-CEACAM8 mAb 80H3 (30 µg/ml) for 5 hours. The percentage of cell survival was assessed by double-staining with FITC-annexin V/propidium iodide and flow cytometry as described in Example 1. Representative results are shown in FIG. 3. The monoclonal antibodies binding to CEACAM1, CEACAM3 or CEACAM6 prevented the apoptotic effect caused by the CEACAM8-binding mAb 80H3 (57 to 62% of viable cells after pre-treatment versus a 42% survival without pre-treatment).

EXAMPLE 4

Figure 5:
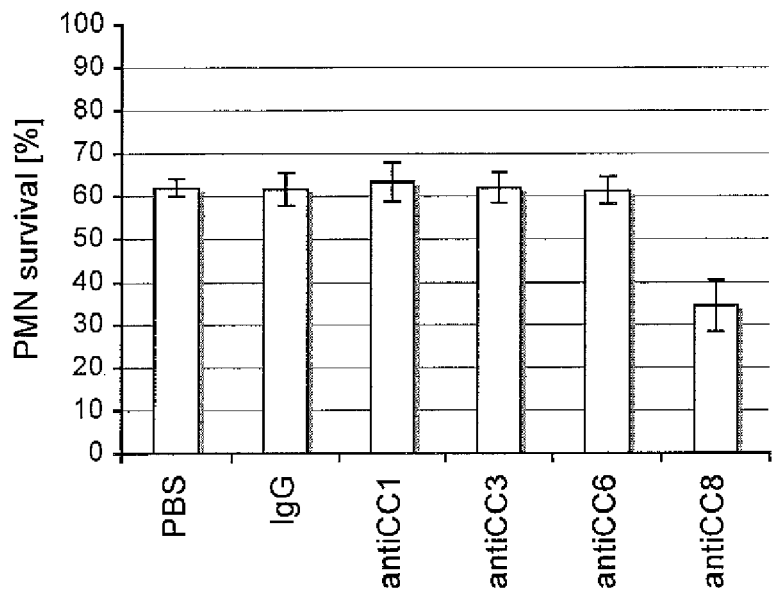
FIG. 5 shows the CEACAM8-triggered induction of apoptosis in human granulocytes isolated from patients suffering arthritis.
Figure 6:
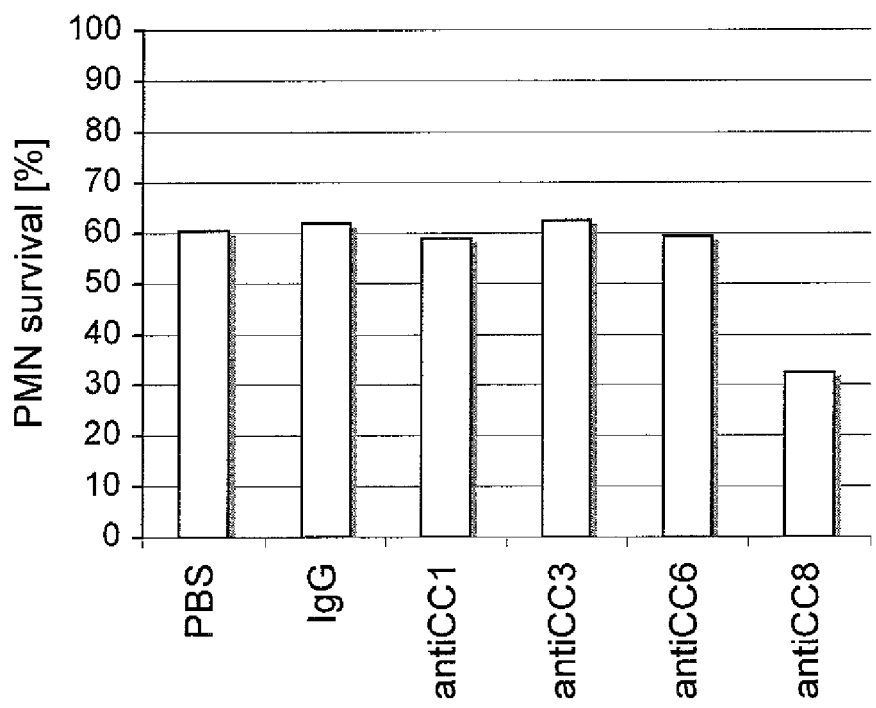
FIG. 6 shows the CEACAM8-triggered induction of apoptosis in human granulocytes isolated from patients suffering psoriasis.

PMNs of patients suffering either psoriasis or severe arthritis were analyzed as follows: Granulocytes were isolated either from peripheral blood (psoriasis) or from synovial fluid of the knee (arthritis) and incubated at 37° C. for 5 to 6 hours with or without the CEACAM8 specific monoclonal antibody mAb 80H3 or monoclonal antibodies specific for CEACAM1 (mAb 4/3/17), CEACAM3 (mAb Col-1), CEACAM6 (mAb 13H10) and an isotype control antibody (30 µg/ml each). In order to determine and distinguish between early and late apoptotic/necrotic cells, a procedure based on double-staining for FITC-annexin V and propidium iodide and flow cytometry was adapted according to Example 1. The results clearly demonstrated that the binding of the CEACAM8-monospecific antibody 80H3 led to a significant induction of apoptosis in human granulocytes isolated from patients suffering either arthritis (FIG. 5) or psoriasis (FIG. 6). Antibodies binding to CEACAM1, CEACAM3, CEACAM6 and the isotype control antibody did not show any effect. This finding agreed with the previous observation in granulocytes primed by injury. As shown in Example 1, the percentage of anti-CEACAM8 induced cell death appeared more remarkable in granulocytes of a patient with severe knee injury than in PMNs isolated from healthy donors.

The invention claimed is:

1. A method for treating a human subject having an autoimmune disease selected from the group consisting of arthritis, arthrosis, autoimmune hepatitis, chronic gastritis, colitis, diabetes mellitus type 1, Morbus Crohn, multiple sclerosis, neurodermatitis, pancreatitis, psoriasis and rheumatism, comprising administering to the subject an effective amount of the monoclonal antibody mAb 80H3 specific to CEACAM8.

2. The method according to claim 1, wherein the autoimmune disease is arthritis, arthrosis, rheumatism or psoriasis.

* * * * *